United States Patent [19]

Scherrer et al.

[11] 3,952,046
[45] Apr. 20, 1976

[54] LIQUID CRYSTALLINE BIPHENYLS
[75] Inventors: Hanspeter Scherrer, Therwil; Arthur Boller, Binningen, both of Switzerland
[73] Assignee: Hoffmann-La Roche Inc., Nutley, N.J.
[22] Filed: Nov. 14, 1974
[21] Appl. No.: 523,594

[52] U.S. Cl. .............................. 260/463; 252/299; 260/465 D; 350/150; 350/160 LC
[51] Int. Cl.² ................. C07C 69/96; C07C 121/64
[58] Field of Search ...................... 260/465 D, 463

[56] References Cited
OTHER PUBLICATIONS
Gray et al., Electron. Lett., Vol. 9, No. 6, pp. 130–131, (1973).

*Primary Examiner*—Lewis Gotts
*Assistant Examiner*—Dolph H. Torrence
*Attorney, Agent, or Firm*—Samuel L. Welt; Bernard S. Leon

[57] ABSTRACT

Liquid crystalline compounds of the formula

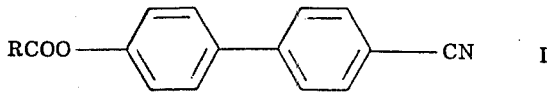

wherein R is as hereinafter set forth, which are useful as dielectrics in electro-optical devices, are described.

16 Claims, No Drawings

LIQUID CRYSTALLINE BIPHENYLS

BRIEF SUMMARY OF THE INVENTION

The invention relates to compounds of the formula

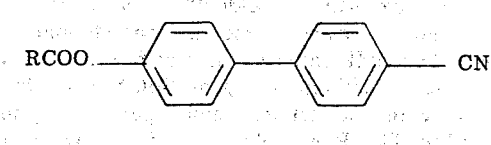

wherein R is straight-chain alkyl of 3 to 8 carbon atoms or straight-chain alkoxy of 3 to 10 carbon atoms.

The compounds of formula I are useful as dielectrics in electro-optical apparatuses.

DETAILED DESCRIPTION OF THE INVENTION

The invention relates to compounds of the formula

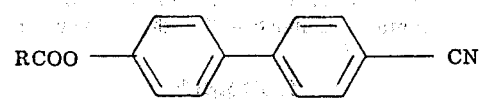

wherein R is straight-chain alkyl of 3 to 8 carbon atoms or straight-chain alkoxy of 3 to 10 carbon atoms.

The compounds of formula I have, in the liquid crystalline state, a positive anisotropy of the dielectric constants, i.e., $\epsilon_\parallel > \epsilon_\perp$, wherein $\epsilon_\parallel$ is the dielectric constant along the longitudinal axis of the molecule and $\epsilon_\perp$ is the dielectric constant perpendicular thereto.

In an electric field the nematic liquid crystals of the invention orientate themselves (because $\epsilon_\parallel > \epsilon_\perp$) in the direction of their largest dielectric constant, that is, with their longitudinal axis, parallel to the direction of the field. This effect is utilized, inter alia, in the interaction between embedded molecules and the liquid crystalline molecules (guest-host interaction) described by J. H. Helmeier and L. A. Zanoni [Applied Physics Letters 13, 91 (1968)]. Another interesting application of the dielectric field orientation is in the rotation cell discovered by M. Schadt and W. Helfrich [Applied Physics Letters 18, 127 (1971)], as well as in the Kerr cell described in Molecular Crystals and Liquid Crystals 17, 355 (1972).

In the electro-optical rotation cell there is present essentially a condenser with transparent electrodes whose dielectric is formed from a nematic substance with $\epsilon_\parallel > \epsilon_\perp$. The longitudinal axes of the molecules of the liquid crystals are arranged in twisted form between the condenser plates in the fieldless state, the twisted structure being determined by the given wall orientation of the molecules. After the application of an electric potential to the condenser plates, the molecules adjust themselves with their longitudinal axes in the field direction, i.e., perpendicular to the surface of the plates, by which means linear polarized light is no longer rotated in the dielectric (the liquid crystal is uniaxially perpendicular to the surface of the plates). This effect is reversible and can therefore be used to control the optical transmissivity of the condenser.

In such a "light rotation cell" it is desirable to use compounds which possess a low melting point, broad nematic range, high stability and slight viscosity. The hitherto used compounds or mixtures with liquid crystalline properties have the disadvantage that at least one of these requirements is not always sufficiently satisfied. It has now surprisingly been found that the compounds of formula I of the invention possess liquid crystalline properties which meet with all of these requirements. They not only have the necessary strong positive anisotropy of the dielectric constants, but, especially in the form of their mixtures with one another or with other other nematic or non-nematic substances, they are liquid crystalline at relatively low temperature, show a slight viscosity, a wide nematic range and a high stability. The operation of electro-optical devices is accordingly possible with lower voltage, shorter susceptibility, i.e., responsive time. Moreover, because of the high stability of the compounds of formula I, they can be handled more readily.

Preferred among the compounds of formula I are those wherein R is alkyl of 4 to 6 carbon atoms. Especially preferred is the compound of formula I wherein R is = n-butyl, i.e., 4'-cyano-4-biphenyl valerate. Also preferred are compounds of formula I wherein R is pentyloxy, heptyloxy or octyloxy.

The compounds of formula I can be prepared as follows:

a. to prepare a compound wherein R is alkyl, a compound of the formula

   II wherein R' is straight-chain alkyl with 3 to 8 carbon atoms and X is a leaving group, is reacted with 4'-cyano-4-hydroxy-biphenyl or an alkali or alkaline earth metal salt thereof; or b. to prepare a compound wherein R is alkoxy, a compound of the formula

   III wherein R" is straight-chain alkoxy with 3 to 10 carbon atoms and X' is halogen, is reacted with 4'-cyano-4-hydroxy-biphenyl or an alkali or alkaline earth metal salt thereof.

As used herein, the term "leaving group" denotes halogen; hydroxy; lower alkoxy, preferably methoxy or ethoxy; alkaoyloxy, preferably

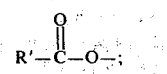

aryl lower alkoxy, preferably benzyloxy; lower alkylsulfonyloxy, preferably mesyloxy; and arylsulfonyloxy, preferably tosyloxy. The term "halogen" denotes fluorine, chlorine, bromine and iodine.

In process embodiment (a) of the invention, 4'-cyano-4-hydroxy-biphenyl or an alkali or alkaline earth metal salt thereof is acylated in a known manner. In principle, there come into consideration all esterifying reactions which are known in the literature, apart from those which are so reactive that the cyano group is concomitantly affected. Preferred, however, are the processes which do not work with an excess of the alcohol reactant.

Thus, 4'-cyano-4-hydroxy-biphenyl can be reacted with a compound of formula II wherein X is halogen, especially chlorine. The reaction is conveniently carried out in an inert organic solvent such as, for example, diethyl ether, tetrahydrofuran, dioxane, methylene chloride, chloroform, benzene, toluene, cyclohexane or the like. In order to bind the hydrogen halide liberated in the reaction, it is convenient to use an acid binding agent. Suitable acid binding agents comprise tertiary amines, pyridines, quinolines or the like. The acid binding agent is preferably used in a large excess so that it can simultaneously serve not only as an acid binding agent but also as the solvent. The reaction is carried out at room temperature or lower temperatures, preferably at 0°–5°C.

An alkali or alkaline earth metal salt of 4'-cyano-4-hydroxy-biphenyl, preferably a sodium, potassium or calcium salt thereof, can also be reacted with a compound of formula II wherein X is halogen—especially chlorine. The reaction is conveniently effected in an inert organic solvent, but it can also be carried out in an aqueous solution.

The compounds of formula II wherein X is chlorine can be obtained, for example, by reaction of the corresponding acid with phosphorus trichloride, phosphorus oxychloride, phosphorus pentachloride or thionyl chloride. The soobtained compound need not be isolated from the reaction mixture prior to the reaction with 4'-cyano-4-hydroxy-biphenyl or an alkali or alkaline earth metal salt thereof.

Furthermore, the 4'-cyano-4-hydroxy-biphenyl can be reacted with a compound of formula II wherein X is alkanoyloxy. Advantageously, there is employed as the compound of formula II the acid anhydride

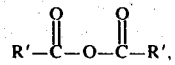

wherein R' is as previously described. Preferably, 4'-cyano-4-hydroxy-biphenyl is warmed with an excess of an acid anhydride under the action of a basic catalyst, for example, sodium acetate or tertiary organic bases, such as pyridine, triethylamine, dimethylaniline, quinoline, or the like; or an acid catalyst such as sulfuric acid or boron trifluoride etherate.

The 4'-cyano-4-hydroxy-biphenyl can also be reacted with a compound of formula II wherein X is alkoxy, especially methoxy or ethoxy. This reaction is conveniently effected in the presence of a small percent of hydrochloric or sulfuric acid and boiling under reflux. This alcoholysis can, however, also be catalyzed by means of a base, for example, using sodium acetate.

Additionally, the 4'-cyano-4-hydroxy-biphenyl can be reacted with a compound of formula II wherein X is hydroxy. This esterification can be effected in the presence of an acid-binding additive such as calcium carbide, calcium hydride, calcium, magnesium, iron, nickel or copper sulfate, or potassium pyrosulfate. A carbodiimide—preferably in the presence of pyridine—can also be used as the acid-binding additive. Finally, this esterification can also be effected in the presence of catalytic amounts of a proton-donating agent, for example, Lewis acid, such as sulfuric acid, hydrochloric acid, toluenesulfonic acid, chlorosulfonic acid or boron trifluoride.

In process embodiment (b) of the invention, 4'-cyano-4-hydroxy-biphenyl is reacted with a compound of formula III wherein X is halogen—especially chlorine. The reaction is conveniently carried out in an inert organic solvent such as diethyl ether, tetrahydrofuran, dioxane, methylene chloride, chloroform, benzene, toluene, or cyclohexane. In order to bind the hydrogen halide liberated in the reaction, it is convenient to use an acid-binding agent. Suitable acid-binding agents comprise tertiary amines, pyridines, quinolines, and the like. Preferably, the acid-binding agent is used in large excess so that it can simultaneously serve not only as the acid-binding agent but also as the solvent. The reaction is carried out at room temperature or lower temperatures, preferably 0°–5°C.

An alkali or alkaline earth metal salt of 4'-cyano-4-hydroxy-biphenyl, preferably a sodium, potassium or calcium salt thereof, can also be reacted with a compound of formula III wherein X' is halogen—especially chlorine. The reaction is conveniently effected in an inert organic solvent, but it can also be carried out in an aqueous solution.

The physical properties of the compounds of formula I of the invention are illustrated in the following Table I:

TABLE I

| R | Melting Point (m.p.) °C | Clearing Point (Cl.p.) °C. | |
|---|---|---|---|
| n-Propyl | 77.9–78.2 | 74.7 | a) |
| n-Butyl | 36.5–36.9 | 61.7 | |
| n-Pentyl | 56.1 | 70.7 | |
| n-Hexyl | 57.7–57.9 | 68.8 | |
| n-Heptyl | 77.5–77.9 | 74.1 | a) |
| n-Octyl | 43.2–43.6 | 74.0 | b) |
| n-Propyloxy | 70.2–70.9 | 68.2 | a) |
| n-Butyloxy | 64.8–65.7 | 64.3 | a) |
| n-Pentyloxy | 50.1–51.0 | 61.1 | |
| n-Hexyloxy | 87.1–87.5 | 62.7 | a) |
| n-Heptyloxy | 50.2–50.5 | 65.2 | |
| n-Octyloxy | 51.6–52.4 | 67.7 | |
| n-Nonyloxy | 53.0–53.1 | 70.0 | c) |
| n-Decyloxy | 59.3–60.0 | 74.0 | d) | a) monotrope  b) smectic up to 61.3°
c) smectic up to 68.1°  d) smectic up to 74.0°

The compounds of formula I of the invention can be used in the form of their mixtures with one another, mixtures which correspond to a eutectic are especially preferred.

The compounds of formula I of the invention are preferably used in the form of their mixtures with other nematic or non-nematic substances such as, for example, with Schiff's bases of the formula

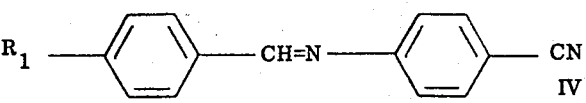

wherein $R_1$ is straight-chain alkyl of 2 to 8 carbon atoms, straight-chain alkoxy of 4 to 7 carbon atoms, straight-chain alkanoyloxy of 2 to 8 carbon atoms or straight-chain alkylcarbonate of 2 to 11 carbon atoms.

Furthermore, the compounds of formula I of the invention can also be used in the form of their mixtures with compounds of the formula

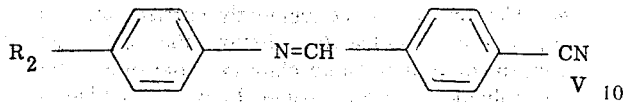
V wherein $R_2$ is straight-chain alkyl of 4 to 7 carbon atoms or straight-chain alkylcarbonate of 2 to 11 carbon atoms, or with compounds of the formula

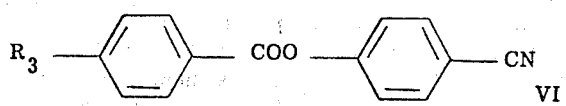
VI wherein $R_3$ is straight-chain alkyl of 4 to 8 carbon atoms, straight-chain alkoxy with 5 to 8 carbon atoms or straight-chain alkylcarbonate with 3 to 11 carbon atoms, or with compounds of the formula

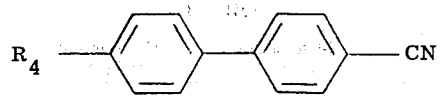
VII wherein $R_4$ is straight-chain alkyl such as, for example, n-pentyl, n-hexyl or n-heptyl or straight-chain alkoxy, such as, for example, n-pentyloxy, n-hexyloxy or n-heptyloxy.

The compounds of formula IV wherein $R_1$ is straight-chain alkylcarbonate are novel and can be manufactured by condensation of a compound of the formula

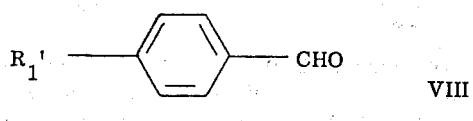
VIII wherein $R_1'$ is a straight-chain alkylcarbonate of 2 to 11 carbon atoms, with p-aminobenzonitrile.

The compounds of formula V wherein $R_2$ is straight-chain alkylcarbonate are likewise novel and can be prepared by condensation of

IX wherein $R_2'$ is a straight-chain alkylcarbonate of 2 to 11 carbon atoms, with p-cyanobenzaldehyde.

The compounds of formula VI wherein $R_3$ is straight-chain alkylcarbonate are likewise novel and can be prepared by reaction of a compound of the formula

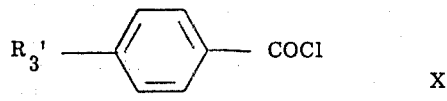
X wherein $R_3'$ is a straight-chain alkylcarbonate of 3 to 11 carbon atoms, with p-hydroxybenzonitrile.

Especially preferred are the following mixtures:
33.3 Mol-% 4'-cyano-4-biphenylyl pentyl carbonate with
33.3 Mol-% 4'-cyano-4-biphenylyl heptyl carbonate and
33.3 Mol-% 4'-n-hexyl-4-cyanobiphenyl, m.p. 6.6°C., cl.p. 51°C;
50 Mol-% 4'-cyano-4-biphenylyl heptyl carbonate and
50 Mol.-% p-n-heptylbenzoic acid p'-cyanophenyl ester, m.p. −2°C, cl.p. 58°C;
33.3 Mol-% 4'-cyano-4-biphenylyl pentyl carbonate with
33.3 Mol-% 4'-cyano-4-biphenylyl octyl carbonate and
33.3 Mol-% 4'-n-hexyl-4-cyanobiphenyl, m.p. < −20°C, cl.p. 51°C;
33.3 Mol-% 4'-cyano-4-biphenylyl octyl carbonate with
33.3 Mol-% 4'-cyano-4-biphenylyl pentyl carbonate and
33.3 Mol-% 4'-n-heptyl-4-cyanobiphenyl, m.p. < −20°C, cl.p. 55°C;
33.3 Mol-% 4'-cyano-4-biphenylyl octyl carbonate with
33.3 Mol-% 4'-cyano-4-biphenylyl hexanoate and
33.3 Mol-% 4'-n-heptyl-4-cyanobiphenyl, m.p. < −20°C, cl.p. 58°C;
33.3 Mol-% 4'-cyano-4-biphenylyl octyl carbonate with
33.3 Mol-% p-(p-cyanophenoxy)carbonyl phenyl n-heptyl carbonate and
33.3 Mol-% 4'-n-heptyl-4-cyanobiphenyl, m.p. 17°C, cl.p. 59°C;
33.3 Mol-% 4'-cyano-4-biphenylyl octyl carbonate with
33.3 Mol-% 4'-cyano-4-biphenylyl hexanoate and
33.3 Mol-% p-(p-hexylbenzyliden)amino benzonitrile, m.p. < −20°C, cl.p. 66.5°C;
33.3 Mol-% 4'-cyano-4-biphenylyl octyl carbonate with
33.3 Mol-% 4'-cyano-4-biphenylyl pentyl carbonate and
33.3 Mol-% p-(p-n-hexylbenzyliden)amino benzonitrile, m.p. < −20°C, cl.p. 66°C;
33.3 Mol-% 4'-cyano-4-biphenylyl octyl carbonate with
33.3 Mol-% 4'-cyano-4-biphenylyl valerate and
33.3 Mol-% p-(p-propylbenzyliden)amino benzonitrile, m.p. < −20°C, cl.p. 65°C.

The preparation of the compounds of formula I as well as the compounds of formulas IV, V and VI wherein $R_1$, $R_2$ or $R_3$ is straight-chain alkylcarbonate is illustrated by the following Examples. All temperatures are given in degrees Centigrade, unless otherwise specified.

EXAMPLE 1

Preparation of 4'-cyano-4-biphenylyl butyrate 0.390 G. of 4'-cyano-4-hydroxy-biphenyl are dissolved in 4.0 ml. of absolute pyridine and cooled to −10° with stirring. 0.255 G. of butyric acid chloride are added dropwise thereto over a period of 2 minutes. The temperature rises to 0° and pyridine hydrochloride precipitates out. Subsequently, the mixture is stirred overnight at room temperature and the suspension poured on to a mixture of 12 g. of ice and 12 ml. of 20% hydrochloric acid. Thereafter, this mixture is extracted three times with ethyl acetate, washed with water, dried over sodium sulfate and evaporated in vacuum. The 0.552 g. of yellowish crystals obtained as the residue are dissolved in benzene and chromatographed on 40 g. of silica gel. Benzene elutes 0.521 g. of yellowish crystals which are recrystallized from acetone-hexane up to constant melting point and clearing point. The pure 4'-cyano-4-biphenylyl butyrate obtained melts at 77.9°–78.2° and is liquid crystalline (monotrope) upon cooling to 74.7°. UV (EtOH): $\epsilon_{272} = 26,100$.

EXAMPLE 2

Preparation of 4'-cyano-4-biphenylyl valerate 0.390 G. of 4'-cyano-4-hydroxy-biphenyl are dissolved in 4.0 ml. of absolute pyridine and reacted with 0.289 g. of valeric acid chloride as in Example 1. The 0.590 g. of brownish colored turbid oil obtained according to the procedure described in Example 1 are dissolved in benzene and chromatographed on 40 g. of silica gel. Benzene elutes 0.518 g. of a colorless, turbid oil which crystallizes upon trituration. It is recrystallized from acetone-hexane up to constant melting point and clearing point. The pure 4'-cyano-4-biphenylyl valerate obtained melts at 36.5°–36.9° and has a clearing point of 61.7°. UV (EtOH): $\epsilon_{271} = 25,800$.

EXAMPLE 3

Preparation of 4'-cyano-4-biphenylyl hexanoate 0.390 G. of 4'-cyano-4-hydroxy-biphenyl are dissolved in 4.0 ml. of absolute pyridine and reacted with 0.323 g. of caproic acid chloride as in Example 1. The 0.613 g. of yellowish crystals obtained according to the procedure described in Example 1 are dissolved in benzene and chromatographed on 40 g. of silica gel. Benzene elutes 0.555 g. of colorless crystals which are recrystallized from acetone-hexane up to constant melting point and clearing point. The pure 4'-cyano-4-biphenylyl hexanoate obtained melts at 56.1° and has a clearing point of 70.7°. UV (EtOH): $\epsilon_{273} = 26,400$.

EXAMPLE 4

Preparation of 4'-cyano-4-biphenylyl heptanoate 0.390 G. of 4'-cyano-4-hydroxy-biphenyl are dissolved in 4.0 ml. of absolute pyridine and reacted with 0.356 g. of oenanthic acid chloride as in Example 1. The 0.671 g. of yellow crystals obtained according to the procedure described in Example 1 are dissolved in benzene and chromatographed on 40 g. of silica gel. Benzene elutes 0.581 g. of colorless crystals which are recrystallized from acetone-hexane up to constant melting point and clearing point. The pure 4'-cyano-4-biphenylyl heptanoate obtained melts at 57.7°–57.9° and has a clearing point of 68.8°. UV (EtOH): $\epsilon_{272} = 26,800$.

EXAMPLE 5

Preparation of 4'-cyano-4-biphenylyl octanoate 0.390 G. of 4'-cyano-4-hydroxy-biphenyl are dissolved in 4.0 ml. of absolute pyridine and reacted with 0.390 g. of caprylic acid chloride as in Example 1. The 0.671 g. of yellowish crystals obtained according to the procedure described in Example 1 are dissolved in benzene and chromatographed on 40 g. of silica gel. Benzene elutes 0.586 g. of colorless crystals which are recrystallized from acetone-hexane up to constant melting point and clearing point. The pure 4'-cyano-4-biphenylyl octanoate obtained melts at 77.5°–77.9° and is liquid crystalline (monotrope) upon cooling to 74.1°. UV (EtOH): $\epsilon_{272} = 26,500$.

EXAMPLE 6

Preparation of 4'-cyano-4-biphenylyl nonanoate 0.390 G. of 4'-cyano-4-hydroxy-biphenyl are dissolved in 4.0 ml. of absolute pyridine and reacted with 0.424 g. of pelargonic acid chloride as in Example 1. The 0.722 g. of yellow crystals obtained according to the procedure described in Example 1 are dissolved in benzene and chromatographed on 40 g. of silica gel. Benzene elutes 0.617 g. of colorless crystals which are recrystallized from acetone-hexane up to constant melting point and clearing point. The pure 4'-cyano-4-biphenylyl nonanoate obtained melts at 43.2°–43.6° and has a clearing point of 74.0°. The compound is smectic up to 61.3°. UV (EtOH): $\epsilon_{272} = 26,900$.

EXAMPLE 7

Preparation of 4'-cyano-4-biphenylyl n-propyl carbonate 0.390 G. of 4'-cyano-4-hydroxy-biphenyl are dissolved in 4.0 ml. of absolute pyridine and reacted with 0.293 g. of chloroformic acid n-propyl ester as in Example 1. The 0.546 g. of brownish crystals obtained according to the procedure described in Example 1 are dissolved in benzene and chromatographed on 40 g. of silica gel. Benzene elutes 0.528 g. of yellowish crystals which are recrystallized from ether-hexane up to constant melting point and clearing point. The pure 4'-cyano-4-biphenylyl n-propyl carbonate obtained melts at 70.2°–70.9° and is liquid crystalline (monotrope) upon cooling to 68.2°. UV (EtOH): $\epsilon_{270} = 26,000$.

EXAMPLE 8

Preparation of 4'-cyano-4-biphenylyl n-butyl carbonate 0.390 G. of 4'-cyano-4-hydroxy-biphenyl are dissolved in 4.0 ml. of absolute pyridine and reacted 0.328 g. of chloroformic acid n-butyl ester as in Example 1. The 0.579 g. of colorless oil obtained according to the procedure described in Example 1 crystallizes after trituration. The crystals are dissolved in benzene and chromatographed on 40 g. of silica gel. Benzene elutes 0.521 g. of colorless crystals which are recrystallized from ether/hexane up to constant melting point and clearing point. The pure 4'-cyano-4-biphenylyl n-butyl carbonate obtained melts at 64.8°–65.7° and is liquid crystalline (monotrope) upon cooling to 64.3°. UV (EtOH): $\epsilon_{270} = 26,300$.

EXAMPLE 9

Preparation of 4'-cyano-4-biphenylyl n-pentyl carbonate 0.976 G. of 4'-cyano-4-hydroxy-biphenyl are dissolved in 10 ml. of absolute pyridine and reacted with 0.90 g. of chloroformic acid n-pentyl ester as in Example 1. The 1.5 g. of yellow, partially crystallized oil obtained according to the procedure described in Example 1 is dissolved in benzene and chromatographed on 90 g. of silica gel. Benzene elutes 1.479 g. of colorless crystals which are recrystallized from ether-hexane up to constant melting point and clearing point. The pure 4'-cyano-4-biphenylyl n-pentyl carbonate obtained melts at 50.1°–51.0° and has a clearing point of 61.1°. UV (EtOH): $\epsilon_{270} = 26,800$.

EXAMPLE 10

Preparation of 4'-cyano-4-biphenylyl n-hexyl carbonate 0.976 G. of 4'-cyano-4-hydroxy-biphenyl are dissolved in 10 ml. of absolute pyridine and reacted with 0.988 g. of chloroformic acid n-hexyl ester as in Example 1. The 1.675 g. of yellowish, turbid, partially crystallized oil obtained according to the procedure described in Example 1 is dissolved in benzene and chromatographed on 80 g. of silica gel. Benzene elutes 1.530 g. of colorless crystals which are recrystallized from ether-hexane up to constant melting point and clearing point. The pure 4'-cyano-4-biphenylyl n-hexyl carbonate obtained melts at 87.1°–87.5° and is liquid crystalline (monotrope) upon cooling to 62.7°. UV (EtOH): $\epsilon_{270} = 26,300$.

EXAMPLE 11

Preparation of 4'-cyano-4-biphenylyl n-heptyl carbonate 0.976 G. of 4'-cyano-4-hydroxy-biphenyl are dissolved in 10 ml. of absolute pyridine and reacted with 1.07 g. of chloroformic acid n-heptyl ester as in Example 1. The 1.8 g. of yellow oil obtained according to the procedure described in Example 1 is dissolved in benzene and chromatographed on 90 g. of silica gel. Benzene elutes 1.782 g. of colorless crystals which are recrystallized from ether-hexane up to constant melting point and clearing point. The pure 4'-cyano-4-biphenylyl n-heptyl carbonate obtained melts at 50.2°–50.5° and has a clearing point of 65.2°. UV (EtOH): $\epsilon_{270} = 25,900$.

EXAMPLE 12

Preparation of 4'-cyano-4-biphenylyl n-octyl carbonate 0.390 G. of 4'-cyano-4-hydroxy-biphenyl are dissolved in 10 ml. of absolute pyridine and reacted with 0.423 g. of chloroformic acid n-octyl ester as in Example 1. The 0.721 g. of brownish oil obtained according to the procedure described in Example 1 is dissolved in benzene and chromatographed on 40 g. of silica gel. Benzene elutes 0.620 g. of colorless crystals which are recrystallized from ether-hexane up to constant melting point and clearing point. The pure 4'-cyano-4-biphenylyl n-octyl carbonate obtained melts at 51.64° and has a clearing point of 67.7°. UV (EtOH): $\epsilon_{270} = 26,000$.

EXAMPLE 13

Preparation of 4'-cyano-4-biphenylyl n-nonyl carbonate 0.976 G. of 4'-cyano-4-hydroxy-biphenyl are dissolved in 10 ml. of absolute pyridine and reacted with 1.24 g. of chloroformic acid n-nonyl ester as in Example 1. The 2.026 g. of yellowish, turbid oil obtained according to the procedure described in Example 1 is dissolved in benzene and chromatographed on 90 g. of silica gel. Benzene elutes 1.646 g. of colorless crystals which are recrystallized from ether-hexane up to constant melting point and clearing point. The pure 4'-cyano-4-biphenylyl n-nonyl carbonate obtained melts at 53.0°–53.1° and has a clearing point of 70.0°. The compound is smectic up to 68.1°. UV (EtOH): $\epsilon_{271} = 26,600$.

EXAMPLE 14

Preparation of 4'-cyano-4-biphenylyl n-decyl carbonate 0.384 G. of 4'-cyano-4-hydroxy-biphenyl are dissolved in 3.2 ml. of absolute pyridine and reacted with 0.527 g. of chloroformic acid n-decyl ester as in Example 1. The 0.822 g. of brownish crystals obtained according to the procedure described in Example 1 are dissolved in benzene and chromatographed on 40 g. of silica gel. Benzene elutes 0.714 g. of colorless crystals which are recrystallized from ether-hexane up to constant melting point and clearing point. The pure 4'-cyano-4-biphenylyl n-decyl carbonate obtained melts at 59.3°–60.0° and has a clearing point of 74.0°. The compound is smectic in the entire liquid crystalline range. UV (EtOH): $\epsilon_{270} = 26,400$.

EXAMPLE 15

Preparation of p-[N-(p-cyanophenyl)formimidoyl]phenyl methyl carbonate

A mixture of 6.1 g. of p-formylphenylcarbonic acid methyl ester and 4.0 g. of p-aminobenzonitrile is gassed with argon in 100 ml. of benzene and heated under reflux for 1 hour (bath temperature 135°). The resulting water is separated with a water separator. During an additional hour, the benzene condensed in the reflux condenser is led back into the reaction vessel through a layer of 100 g. of aluminium oxide (act. I). After cooling, the mixture is freed from solvent in vacuum at 50° bath temperature, whereby there remain 9.3 g. of practically colorless crystals which are recrystallized several times from isopropanol up to constant melting point and clearing point and up to the disappearance of side-products in the gas chromatogram. The pure colorless p-[N-(p-cyanophenyl)-formimidoyl]phenyl methyl carbonate obtained has a melting point of 139.0°–139.2° and a clearing point of 156.0°. UV (EtOH): $\epsilon_{274} = 24,100$ (shoulders at 315 and 234 nm; minimum at 242 nm).

EXAMPLE 16

Preparation of p-[(p-cyanobenzyliden)amino]phenyl methyl carbonate

A mixture of 0.835 g. of p-methoxycarbonyloxyaniline and 0.655 g. of p-cyanobenzaldehyde is gassed with argon in 50 ml. of benzene and heated under reflux for 1 hour (bath temperature 130°). The resulting water is separated with a water separator. During an additional hour, benzene condensed in the reflux condenser is now passed back into the reaction vessel through a layer of 20 g. of aluminium oxide (act. I). After cooling, the reaction mixture is freed from solvent in vacuum at 50°C. bath temperature, whereby there remain 1.395 g. of yellowish crystals which are recrystallized several times from isopropanol up to constant melting point and clearing point and up to the disappearance of side-products in the gas chromatogram. The pure, slightly yellowish p-[(p-cyanobenzyliden)amino]phenyl methyl carbonate obtained has a melting point of 145.1°–146.2° and a clearing point of 163.4°. UV (EtOH): $\epsilon_{270} = 20,250$, $\epsilon_{324} = 10,800$ (shoulders at 243 and 221 nm; minima at 312 and 233 nm).

EXAMPLE 17

Preparation of p-[(p-cyanophenoxy)carbonyl]phenyl ethyl carbonate 5.66 G. of p-cyanophenol are dissolved in 66 ml. of absolute pyridine and cooled to −10° with stirring. A total of 8.6 g. of crude p-carbethoxy-oxybenzoyl chloride is then added portionwise thereto over a period of 10 minutes. The temperature rises to 0° and pyridine hydrochloride precipitates out. The mixture is stirred overnight at room temperature and the suspension poured on to a mixture of 200 ml. of ice and 200 ml. of 20% hydrochloric acid. Thereafter, this mixture is extracted three times with ethyl acetate, washed with water, dried over sodium sulfate and evaporated under vacuum. The 12.4 g. of reddish crystals obtained as the residue are dissolved in benzene and chromatographed on 400 g. of silica gel. Benzene-1% acetone (v/v) elute 8.1 g. of yellowish crystals which are recrystallized from acetone-hexane up to constant melting point and clearing point. The pure p-[(p-cyanophenoxy)carbonyl]phenyl ethyl carbonate obtained melts at 144.7°–144.8° and is liquid crystalline (monotrope) upon cooling to 115.8°. UV (EtOH): $\epsilon_{241} = 29,700$.

The starting material is prepared as follows:

Chloroformic acid ethyl ester is allowed to act on p-hydroxybenzoic acid in the presence of N-caustic soda according to the method of E. Fischer, Ber. 41, 2877 (1908), whereby there is obtained crystalline p-carbethoxy-oxybenzoic acid which is treated with thionyl chloride according to the data of H. Schonenberger et al. Arzneimittelforschung 14, 324 (1964). After removal of the excess thionyl chloride in vacuum, there is obtained crude p-carbethoxy-oxybenzoyl chloride which is then reacted directly as described above.

We claim:

1. A compound of the formula

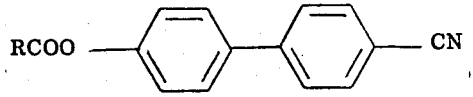

wherein R is straight-chain alkyl of 3 to 8 carbon atoms or straight-chain alkoxy of 3 to 10 carbon atoms.

2. A compound in accordance with claim 1, wherein R is n-butyl, n-pentyl, n-hexyl, n-pentyloxy, n-heptyloxy or n-octyloxy.

3. The compound in accordance with claim 1, 4'-cyano-4-biphenylyl butyrate.

4. The compound in accordance with claim 1, 4'-cyano-4-biphenylyl valerate.

5. The compound in accordance with claim 1, 4'-cyano-4-biphenylyl hexanoate.

6. The compound in accordance with claim 1, 4'-cyano-4-biphenylyl octanoate.

7. The compound in accordance with claim 1, 4'-cyano-4-biphenylyl nonanoate.

8. The compound in accordance with claim 1, 4'-cyano-4-biphenylyl n-propyl carbonate.

9. The compound in accordance with claim 1, 4'-cyano-4-biphenylyl n-butyl carbonate.

10. The compound in accordance with claim 1, 4'-cyano-4-biphenylyl n-pentyl carbonate.

11. The compound in accordance with claim 1, 4'-cyano-4-biphenylyl n-hexyl carbonate.

12. The compound in accordance with claim 1, 4'-cyano-4-biphenylyl n-heptyl carbonate.

13. The compound in accordance with claim 1, 4'-cyano-4-biphenylyl n-octyl carbonate.

14. The compound in accordance with claim 1, 4'-cyano-4-biphenylyl n-nonyl carbonate.

15. The compound in accordance with claim 1, 4'-cyano-4-biphenylyl n-decyl carbonate 16. The compound in accordance with claim 1, 4'-cyano-4-biphenylyl heptanoate.

* * * * *

UNITED STATES PATENT AND TRADEMARK OFFICE
CERTIFICATE OF CORRECTION

PATENT NO. : 3,952,046
DATED : April 20, 1976
INVENTOR(S) : Arthur Boller & Hanspeter Scherrer It is certified that error appears in the above-identified patent and that said Letters Patent are hereby corrected as shown below:

Cover Sheet, after
"[21] Appl. No.: 523,594" insert

[30] Foreign Application Priority Data

November 19, 1973        Switzerland        No. 16242/73

Signed and Sealed this

Twenty-fourth Day of August 1976

[SEAL]

Attest:

RUTH C. MASON
*Attesting Officer*

C. MARSHALL DANN
*Commissioner of Patents and Trademarks*